United States Patent
Dalpiaz et al.

(10) Patent No.: US 7,580,502 B2
(45) Date of Patent: Aug. 25, 2009

(54) SYSTEM AND METHOD FOR POSITIONING DENTAL DIGITAL X-RAY APPARATUS

(75) Inventors: Michael Dalpiaz, Zwingenberg (DE); Ulrich Schulze-Ganzlin, Lorsch (DE); Werner Günther, Bensheim (DE); Jürgen Zimmermann, Biebesheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 712 days.

(21) Appl. No.: 10/644,992

(22) Filed: Aug. 21, 2003

(65) Prior Publication Data

US 2005/0031086 A1    Feb. 10, 2005

Related U.S. Application Data

(63) Continuation of application No. PCT/DE02/00636, filed on Feb. 21, 2002.

(51) Int. Cl.
*A61B 6/14* (2006.01)
*G01N 23/083* (2006.01)

(52) U.S. Cl. .............................. 378/40; 378/38; 378/39; 378/62

(58) Field of Classification Search .................. 378/38, 378/39, 40, 62, 196, 197, 16, 98.7, 108–112
See application file for complete search history.

(56) References Cited

U.S. PATENT DOCUMENTS

| | | | |
|---|---|---|---|
| 4,813,060 A | 3/1989 | Heubeck et al. | 378/39 |
| 4,847,881 A | 7/1989 | Heubeck | 378/38 |
| 4,856,038 A * | 8/1989 | Guenther et al. | 378/39 |
| 5,511,106 A | 4/1996 | Doebert et al. | 378/146 |
| 5,513,252 A | 4/1996 | Blaschka et al. | 378/98.8 |
| 5,963,003 A * | 10/1999 | Boyer | 318/574 |
| 6,050,724 A | 4/2000 | Schmitz et al. | 378/205 |
| 6,055,292 A | 4/2000 | Zeller et al. | 378/21 |
| 6,233,310 B1 * | 5/2001 | Relihan et al. | 378/108 |
| 6,463,121 B1 * | 10/2002 | Milnes | 378/62 |
| 6,619,839 B2 * | 9/2003 | Yoshimura | 378/196 |
| 6,793,391 B2 * | 9/2004 | Zimmermann | 378/205 |

* cited by examiner

*Primary Examiner*—Allen C. Ho
(74) *Attorney, Agent, or Firm*—Dykema Gossett PLLC

(57) ABSTRACT

An arrangement for positioning an X-ray machine, with an input and an output device, for interactive control, with a memory region, in which digitised X-ray images and X-ray machine data are stored, an interface, by means of which information is exchanged with the X-ray machine, a pointing device for selecting regions in digitized X-ray images, a processing unit, which carries out calculations based on the digitized X-ray images, the associated X-ray machine data and the selected region, in order to determine control data such that the X-ray machine is controlled whereby, on taking an image, the selected region is screened.

27 Claims, 2 Drawing Sheets

SYSTEM AND METHOD FOR POSITIONING DENTAL DIGITAL X-RAY APPARATUS

CROSS REFERENCE TO RELATED APPLICATION

This is a continuation of International Application PCT/DE02/00636 filed Feb. 21, 2002, which designated the U.S. All priorities are claimed.

TECHNICAL FIELD

The invention relates to a system and method for positioning digital dental X-ray apparatus. In dentistry, much time is spent on positioning X-ray apparatus. The practitioner must comply with a fixed sequence of operations. In one possible sequence of operations he might pass from a large-area photograph (eg, panoramic image) to smaller images (for example an intraoral image of a detail or some other tomographic image of details, eg, individual teeth). Determination of the detail area is carried out on the basis of the general image (panoramic image).

BACKGROUND OF THE INVENTION

X-ray apparatus for making panoramic radiograms and individual images therefrom is disclosed in DE 3 545 509 (U.S. Pat. No. 4,847,881) and DE 3 545 493 (U.S. Pat. No. 4,813,060). Digital X-ray images for panoramic radiograms and cephalometric images are disclosed in EP 0 632 994 (U.S. Pat. No. 5,511,106). The production of digital intraoral images using an intraoral sensor is disclosed in EP 0 643 901 (U.S. Pat. No. 5,513,252). The features disclosed in these documents are incorporated in this application by reference.

Instructions for further investigation are usually passed on verbally or in writing.

DE 197 03 556 A1 discloses a method of positioning radiographic apparatus in which at least one X-ray image of an object to be examined is produced using X-ray apparatus. The X-ray apparatus is provided with a detector system, by means of which the position of marking means disposed on the object to be examined or at a fixed position relative to the object to be examined is registered in a detector coordinate system that is coupled to the detector system. The position of the X-ray apparatus is determined in an object coordinate system, which is coupled to the object to be examined. Then the position of a point of the object depicted as a halftone dot in an X-ray image is determined in the object coordinate system. By means of this method the precise assignment of a point in an X-ray image to a point in or near the object to be examined is possible. Furthermore, exact positioning of a treatment instrument is also possible.

It is an object of the invention to provide a system and method making it possible to obtain images of details in an efficient manner.

SUMMARY OF THE INVENTION

This object is achieved by a system and a method comprising the features defined in the independent claims.

In particular, this object is achieved by a system for positioning X-ray apparatus, which system exhibits input and output devices for interactive control. The input and output devices provide the user with means for controlling the system. These devices are preferably a keyboard and a display monitor, which are used in conjunction with a pointing device for specifying areas. In one storage area there is stored at least one digitized, preferably single, X-ray image and information concerning the X-ray apparatus. The information concerning the X-ray apparatus is stored in relation to the X-ray image. This makes it possible to assign areas of an X-ray image to certain information concerning the X-ray apparatus. This information concerning the X-ray apparatus preferably relates to position parameters of the movable parts. Thus a certain area of an X-ray image can be associated with the corresponding parameters of the X-ray apparatus. Vice versa, the X-ray apparatus can be controlled by the X-ray image.

The system also has a computer interface, via which information can be exchanged with the X-ray apparatus. In order to specify the area to be considered for an image of a detail, means are provided for selecting areas in the digitized X-ray image. Said means preferably comprise a pointing device, by means of which areas already saved can be selected or by means of which areas not yet created can be specified. This pointing device can be a mouse, for example, by means of which an area can be specified or drawn.

Another component of the present invention is a processing unit, which carries out calculations on the basis of the digitized, preferably individual X-ray image, the associated information concerning the X-ray apparatus and the selected area in order to ascertain control data for steering the X-ray apparatus to make it cover the selected area. These calculations are preferably based on the path information, which, as described above, has been assigned to the imaging information. The path information gives knowledge of the movement of the X-ray apparatus carried out at a certain point of time. Thus the coordinates of the X-ray apparatus are given in relation to a certain point of time.

From current and voltage parameters it is possible to determine the intensity of the radiation both from the radiation source and from the sensor. This allows conclusions to be drawn regarding the image information.

In addition, the representation of potentials as gray tones, in which the X-ray image is represented, tends to be faulty. In order to by-pass this source of error, is it necessary to possess knowledge of the image. By this means deviations can be eliminated by computation.

In a preferred embodiment, the calculation carried out to determine the control data takes account of the type of examination and the purpose of diagnosis as determined during clinical inquiries. The two together give the type of image. Thus the parameters of the X-ray apparatus must be set differently when a root is to be examined from when inspection of a caries affection is to be carried out, since the latter mainly involves the surface of the tooth.

Patient-dependent data, such as size, weight, type, race, age, jaw shape, and previous treatments, may also be taken into account when discerning the control data for the X-ray apparatus. For example, radiation must be set lower for a small child's dentition.

In order to simplify the use of the system as far as possible, the teeth may be recognized by pattern recognition algorithms in advance so that the user only has to select the teeth for which he requires further images. It is thus not necessary for the user to draw an area manually in the image.

On the basis of statistical and stochastic data it is possible to discern further information regarding the anatomy of the patient, which can in turn be included in the calculation of the control data.

The present invention also relates to a method of positioning X-ray apparatus. In a first step, at least one digitized, preferably individual, X-ray image is loaded and displayed. It is usually displayed by a display unit, in particular a display monitor. A second step involves the determination of the coordinates of areas required to be shown in another X-ray image. Such determination can be carried out either manually by drawing in the areas, or by interactively selecting submitted proposals. In a third step, information concerning the X-ray apparatus is loaded, from which it will be seen what parameters are required for making a new image of the selected area. In a fourth step, calculations are carried out based on the digitized X-ray image, the relevant information concerning the X-ray apparatus, and the selected area, in order to ascertain control data which will steer the X-ray apparatus such that the selected area is imaged. The individual calculation steps have been described above.

The information concerning the X-ray apparatus preferably relates to coordinates of the trajectories stored in relation to the digitized X-ray image. With the aid of this information it is possible to calculate a segment of the trajectory for the selected area.

The calculation can likewise take into account current and voltage parameters which have been stored in relation to the digitized X-ray image.

Furthermore, the operating parameters of the sensor can also be varied, for example its pulse rate, and also the parameters for calculating the X-ray image with reference to the signals coming from the sensor, for example, during read-out of full frames, the overlay taking place in the processing unit for subsequent determination of the sharp layer.

In addition to the patient-dependent data, such as size, weight, type, race, age, jaw shape, and previous treatments, the calculation carried out to determine the control data can take into account the type of examination and the purpose of diagnosis according to clinical inquiries.

Automatic recognition of the areas, particularly the teeth, is made possible by pattern recognition algorithms. However, these areas can be changed or determined manually, if desired.

As in the case of the system, statistical and stochastic linkings of the individual parameters are carried out.

BRIEF DESCRIPTION OF THE DRAWINGS

Below, the invention is explained in greater detail with reference to working examples illustrated diagrammatically in the drawing, in which.

WORKING EXAMPLE

Calculation of the presettings involves the previous position, the previous image, and the previous trajectory. Also required for the calculation is the new object to be examined and the new type of examination. The new settings are calculated in the manner described above. The X-ray apparatus is set on the basis of the parameters thus determined.

In addition to fixing the position of an emitter of the X-ray apparatus, an occlusal device, chin and/or forehead holding means, and/or an ear holder can be positioned so as to hold the patient in a position suitable for making the image. This ensures reproducibility for a subsequent X-ray image for comparison purposes or for following up the procedure. Positioning of the X-ray apparatus and/or the patient also involves detectors connected to the X-ray apparatus for making panoramic radiograms (PAN) or transversal tomograms (TSA) and movable intraoral sensors (IO sensors) optionally using special holders for maintaining their position in the mouth of the patient.

The digitized X-ray image used can, in the simplest type of embodiment, be a standardized X-ray image showing specific partial areas of the teeth, by means of which, together with the general device data, rough adjustment of the X-ray apparatus can be carried out according to the desired image selection.

Figure 1:
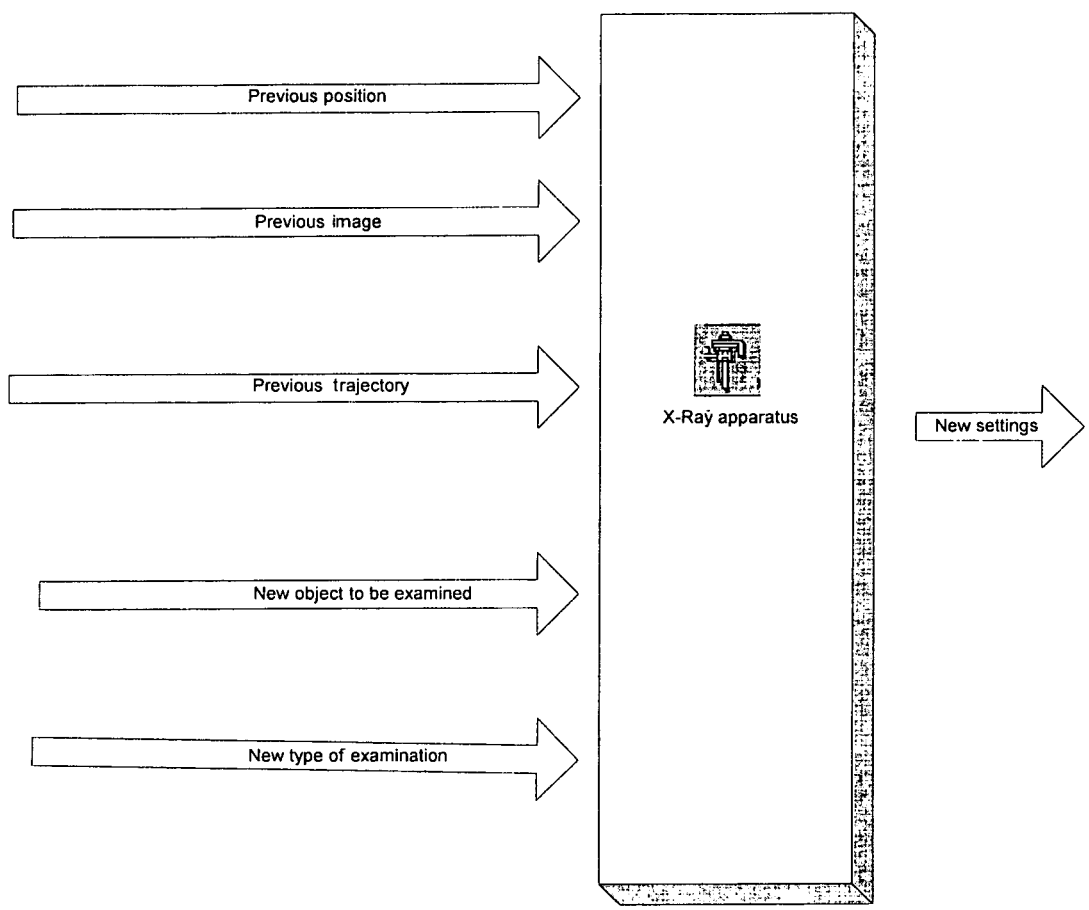
FIG. 1 shows, diagrammatically, the flow of operations involved in determination of the presettings for the X-ray apparatus.
Figure 2:
FIG. 2 shows the automatic selection of an area to be examined with reference to a digitized dental panoramic radiogram.
Figure 3:
FIG. 3 depicts the manual selection of an area to be examined with reference to a digitized dental panoramic radiogram.

FIGS. 2 and 3 show selection possibilities relating to an area to be examined with reference to a digitized dental panoramic radiogram. In the case of FIG. 2, selection of the area is carried out by entering designations of the teeth to be selected or by clicking on the teeth stored as partial areas of the panoramic radiogram, which teeth will then be highlighted. In FIG. 3, the selection of the area is carried out by positioning a selection box, which may simulate the shape and position of an intraoral sensor.

It is particularly advantageous, however, to use existing individual X-ray images of the patient, in which the actual device data used for making the image are saved. Furthermore, an X-ray photograph provided by the patient and used for positioning purposes may exhibit a patient-related association of partial areas so that the selection of the partial area within the patient-related image increases the accuracy of positioning.

It may possibly be necessary to supplement the automatically determined position of the apparatus by manual corrections. These corrections can likewise be stored in the X-ray image together with the image information and thus be available for future images.

The system and the method can be designed such that not only individual images can be made from the selected position but also a series of images can be created starting from the selected position with subsequent adjustments to the position of the X-ray apparatus, for example, when making images of a number of layers of a specific tooth to provide a transversal tomogram. The type of image to be made is chosen prior to calculation of the control data by additional means and is taken into account during computation of the control data. Furthermore, when movable means are provided for positioning the patient, the control data therefor may also be detected or, for the succeeding image, preset.

The method can be set down in the form of a software program as defined in any one or more of the following method claims. A data medium can contain a data structure that is capable of running on a computer to carry a method as defined in one or more of the following method claims into effect.

The invention claimed is:

1. A system for positioning a dental X-ray apparatus, comprising:
    an input and output device for interactive control,
    a storage area, in which at least one panoramic digitized dental X-ray image and information concerning the dental X-ray apparatus assignable to the digitized dental X-ray image are stored,
    a computer interface, via which information can be interchanged with the dental X-ray apparatus,
    means for selecting areas in the digitized dental X-ray image, and
    a processing unit which effects calculations based on the digitized dental X-ray image, the relevant information concerning the dental X-ray apparatus, and the selected area, in order to ascertain control data for controlling the dental X-ray apparatus such that the selected area is covered when a new dental X-ray image is made, the information concerning the X-ray apparatus comprises coordinates of a trajectory which have been saved in relation to the digitized X-ray image, the processing unit further effects calculations of the trajectory which gives knowledge of movement of the dental X-ray apparatus carried out at a certain point of time.

2. A system as defined in claim 1, wherein the digitized X-ray image comprises an individual image of a patient.

3. A system as defined in claim 1, wherein the X-ray apparatus is of a type suitable for various types of image, and wherein means for selecting the type of image are provided.

4. A system as defined in claim 1, further comprising means for positioning a patient relatively to the X-ray apparatus, wherein the control data is adapted to control said means for positioning the patient.

5. A system as defined in claim 1, wherein the storage area includes current and/or voltage parameters saved in relation to the digitized X-ray image.

6. A system as defined in claim 1, wherein the storage area includes information concerning gray tones in the representation of the image saved in relation to the digital X-ray image.

7. A system as defined in claim 1, wherein the processing unit includes computation for determining said control data which takes into account the type of image.

8. A system as defined in claim 1, wherein the processing unit includes computation for determining said control data which takes into account the purpose of diagnosis.

9. A system as defined in claim 1, wherein the processing unit includes patient-dependent data, including one of size, weight, type, race, age, jaw shape, and previous treatments which are taken into account when determining said control data.

10. A system as defined in claim 9, wherein the processing unit includes one of statistical and stochastic linkings of the patient-dependent data.

11. A system as defined in claim 1, further comprising means for automatically recognizing areas by pattern recognition algorithms.

12. A system as defined in claim 11, wherein the areas are teeth.

13. A system as defined in claim 1, wherein the selecting means are designed such that areas can be selected manually.

14. A system as defined in claim 1, further comprising means provided for making a series of radiograms at different positions starting from a selected position.

15. A dental X-ray apparatus including a system as defined in claim 1.

16. A method of positioning one of an emitter and a detector of a dental X-ray apparatus using an existing digitized dental X-ray image and information concerning the dental X-ray apparatus and assignable to the digitized dental X-ray image, comprising the steps of:

loading and displaying at least one panoramic digitized dental X-ray image, determining coordinates of areas, with reference to the digitized dental X-ray image, which are to be depicted in another X-ray image, loading information concerning the dental X-ray apparatus, and carrying out computation on the basis of the digitized X-ray image, relevant information concerning the dental X-ray apparatus, and a selected area, in order to ascertain control data which controls the dental X-ray apparatus such that the selected area can be depicted in a new dental X-ray image, the information concerning the X-ray apparatus comprises coordinates of the trajectory which have been saved in relation to the digitized X-ray image, and a segment of the trajectory is calculated on the basis of the selected area, and the trajectory gives knowledge of movement of the dental X-ray apparatus carried out at a certain point of time.

17. A method as defined in claim 16, wherein the digitized X-ray image comprises an individual image of the patient.

18. A method as defined in claim 16, wherein the type of image to be made by the X-ray apparatus is selected prior to the step of loading information concerning the dental X-ray apparatus.

19. A method as defined in claim 16, wherein the control data is adapted to control means for positioning the patient relative to the X-ray apparatus.

20. A method as defined in claim 16, wherein the computation step includes one of current and voltage parameters which are saved in relation to the digitized X-ray image.

21. A method as defined in claim 16, wherein the computation for determination of the control data takes into account one of the type of examination and the purpose of diagnosis of the patient.

22. A method as defined in claim 16, wherein the patient-dependent data, including one of size, weight, type, race, age, jaw shape, and previous treatments, are taken into account when computing the control data.

23. A method as defined in claim 22, wherein one of statistical and stochastic linkings of the patient-dependent data are carried out.

24. A method as defined in claim 16, wherein the computation step includes automatically recognizing areas by pattern recognition algorithms.

25. A method as defined in claim 24, wherein the areas are teeth.

26. A method as defined in claim 16, wherein the areas can be determined manually.

27. A method as defined in claim 16, further comprising the step of making a series of radiograms at different positions starting from the selected position.

* * * * *